(12) United States Patent
Wilkie

(10) Patent No.: US 7,297,274 B2
(45) Date of Patent: Nov. 20, 2007

(54) FIXED-FILM ANAEROBIC DIGESTION OF FLUSHED WASTE

(75) Inventor: Ann C. Wilkie, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 192 days.

(21) Appl. No.: 10/976,079

(22) Filed: Oct. 28, 2004

(65) Prior Publication Data

US 2005/0167359 A1 Aug. 4, 2005

Related U.S. Application Data

(63) Continuation-in-part of application No. 10/277,486, filed on Oct. 22, 2002, now Pat. No. 6,811,701.

(60) Provisional application No. 60/335,065, filed on Oct. 24, 2001.

(51) Int. Cl.
*C02F 3/28* (2006.01)

(52) U.S. Cl. .................. 210/603; 210/612; 210/615; 210/631; 210/259; 71/10

(58) Field of Classification Search ............. 210/603, 210/609, 612, 613, 615, 631, 150, 151, 252, 210/259; 71/10, 21
See application file for complete search history.

(56) References Cited

U.S. PATENT DOCUMENTS

| | | | | |
|---|---|---|---|---|
| 2,590,964 A | * | 4/1952 | Halvorson | 210/609 |
| 3,329,271 A | * | 7/1967 | Ward et al. | 210/150 |
| 3,402,103 A | | 9/1968 | Herman et al. | |
| 3,589,518 A | * | 6/1971 | Brebion et al. | 210/150 |
| 3,617,541 A | * | 11/1971 | Pan | 210/615 |

(Continued)

FOREIGN PATENT DOCUMENTS

FR  2552298 A1  3/1985

(Continued)

OTHER PUBLICATIONS

Mills, B., "Digester gobbles up odors" *DairyToday*, Jan. 2000, pp. 17-18.

(Continued)

*Primary Examiner*—Fred G. Prince
(74) *Attorney, Agent, or Firm*—Saliwanchik, Lloyd & Saliwanchik

(57) ABSTRACT

An apparatus for the fixed-film anaerobic digestion of flushed livestock manure includes an enclosed digester tank (fixed or flexible roof), internal media for biofilm development, a biogas collection and flare system, various pumps, and hydraulic control systems. The preferred media has substantially vertically-oriented, uninterrupted channels to promote enhanced bacterial attachment and biofilm development. The immobilization of microbial biomass within the reactor as a biofilm allows effective treatment of the wastewater at ambient and higher temperatures, as well as reasonable hydraulic retention times. The composition and concentration of bacterial groups in the biofilm developed on the media in the fixed-film digester result in a significantly enhanced anaerobic degradation process. This novel fixed-film digester design expands the potential application of anaerobic digestion to dilute livestock waste with significant levels of suspended solids. This holistic manure treatment system not only stabilizes the wastewater but also produces energy (biogas), controls odors, reduces pathogens, minimizes environmental impact from waste emissions, and maximizes fertilizer and water recovery for reuse.

22 Claims, 12 Drawing Sheets

U.S. PATENT DOCUMENTS

| | | | |
|---|---|---|---|
| 3,700,590 A * | 10/1972 | Burton | 210/615 |
| 3,846,289 A | 11/1974 | Jeris et al. | |
| 3,956,129 A | 5/1976 | Jeris et al. | |
| 4,009,099 A | 2/1977 | Jeris | |
| 4,026,082 A | 5/1977 | Crofoot | |
| 4,183,809 A | 1/1980 | Klapwijk et al. | |
| 4,284,508 A | 8/1981 | Jewell | |
| 4,366,059 A | 12/1982 | Witt et al. | |
| 4,530,762 A | 7/1985 | Love | |
| 4,561,974 A | 12/1985 | Bernard et al. | |
| 4,599,168 A | 7/1986 | Benjes et al. | |
| 4,604,361 A | 8/1986 | Peters | |
| 4,627,917 A | 12/1986 | Morper | |
| 4,632,758 A | 12/1986 | Whittle | |
| 4,780,198 A | 10/1988 | Crawford et al. | |
| 4,818,404 A * | 4/1989 | McDowell | 210/603 |
| 4,940,540 A * | 7/1990 | McDowell | 210/150 |
| 5,096,579 A | 3/1992 | Jordan et al. | |
| 5,205,935 A | 4/1993 | Ruocco | |
| 5,228,995 A | 7/1993 | Stover | |
| 5,232,585 A | 8/1993 | Kanow | |
| 5,389,248 A | 2/1995 | Pare et al. | |
| 5,419,833 A | 5/1995 | Ely et al. | |
| 5,500,112 A | 3/1996 | McDonald | |
| 5,518,620 A | 5/1996 | Eguchi et al. | |
| 5,560,819 A | 10/1996 | Taguchi | |
| 5,630,942 A | 5/1997 | Steiner | |
| 6,126,816 A | 10/2000 | Ruiz, Jr. | |
| 6,183,643 B1 | 2/2001 | Goodley | |
| 6,217,759 B1 | 4/2001 | Kolesnikov et al. | |
| 6,254,775 B1 | 7/2001 | McElvaney | |
| 6,291,232 B1 | 9/2001 | Miller, III | |
| 6,299,774 B1 | 10/2001 | Ainsworth et al. | |
| 6,398,959 B1 * | 6/2002 | Teran et al. | 210/609 |
| 6,406,630 B1 * | 6/2002 | Henry | 210/612 |
| 6,409,788 B1 * | 6/2002 | Sower | 71/11 |

FOREIGN PATENT DOCUMENTS

| | | | |
|---|---|---|---|
| JP | 61-67474 | * | 4/1987 |
| JP | 1-215397 | * | 8/1989 |

OTHER PUBLICATIONS

Wilkie, A. et al., "Start-up of anaerobic filters containing different support materials using pig slurry supernatant" *Biotechnology Letters*, 1984, vol. 6, No. 11, pp. 735-740.

Wilkie, A. et al., "Pilot-scale digestion of pig slurry supernatant using an upflow anaerobic filter" *Environmental Technology Letters*, vol. 7, pp. 65-76, 1986.

Wilkie, A. et al., "The Development of the Anaeorbic Fixed-Bed Reactor and its Application to the Treatment of Agricultural and Industrial Wastes" *International Biosystems*, 1989, pp. 183-226.

Wilkie et al., "Anaerobic digestion for odor control" *Nuisance Concerns in Animal Manure Management: Odors and Flies*, 1995, pp. 56-62.

"Show Me Results[2] Success Stories from the Florida Energy Office" *Florida Department of Community Affairs*, 1998-99.

Wilkie, A. et al., "Anaerobic digestion: holistic bioprocessing of animal manures" *Proceedings of the Animal Residuals Management Conference*, 2000, pp. 1-12.

Wilkie, A. et al., "Reducing dairy manure odor and producing energy" *Biocycle Journal of Compositing & Organics Recycling*, 2000, pp. 48-50.

Hunter, Ed, "Sweet smell of success: New UF system helps dairy farms reduce odors," *UF News* http://www.napa.ufl.edu/2000news/sweetsme.htm, 2000.

* cited by examiner

FIXED-FILM ANAEROBIC DIGESTION OF FLUSHED WASTE

CROSS-REFERENCE TO RELATED APPLICATION

This application is a continuation-in-part application of U.S. patent application Ser. No. 10/277,486, filed Oct. 22, 2002, now U.S. Pat. No. 6,811,701, which claims the benefit of provisional patent application Ser. No. 60/335,065, filed Oct. 24, 2001, which is hereby incorporated by reference in its entirety.

BACKGROUND OF THE INVENTION

Anaerobic digestion of organic waste has been implemented for many years. In anaerobic digestion, a mixed culture of bacteria mediates the degradation of the putrescible fraction of organic matter ultimately to methane, carbon dioxide and mineralized nutrients. Upon storage, organic waste will naturally begin this process of degradation, resulting in the production of intermediate compounds, which are volatile and often a source of odors. Since methanogenic microorganisms grow slowly and are present in limited numbers in fresh manure, these volatile intermediates accumulate in stored manure. In an effective anaerobic digester, the growth of methanogens is promoted such that the intermediate compounds are converted to biogas and nutrients, and the odor potential of the waste is greatly reduced.

The principal means for promoting methanogenic growth in anaerobic digestion of organic waste are controlling the operating temperature and/or controlling the residence time of the bacteria within the process. The types of anaerobic digester that have been implemented in the digestion of organic waste, in particular agricultural waste such as manure, are rather limited due to the nature of the waste, in particular manure, as a substrate.

Types of anaerobic digesters available for bioprocessing of organic wastes include plug-flow digesters, complete-mix digesters, covered lagoons and a few demonstrations of mixed reactors with flexible-film support media (U.S. Pat. Nos. 5,096,579; 6,254,775), all of which are variations of batch and semi-continuous processes. Except for covered lagoons, these anaerobic digesters are usually operated at mesophilic temperatures (usually 35° C.), which requires energy input. Often a portion of the biogas is used to heat the waste slurry to the operating temperature. The requirement for heating dictates that the waste slurry fed to these reactors should have as high a total solids (TS) content as possible to minimize the water content which must be heated. In practice, the waste slurry added to these heated digesters should have a TS content of 4-12%. In temperate climates, often waste slurry with 1% TS or less will fail to provide enough biogas to heat the slurry to 35° C.

Without any support media for bacterial residence/attachment, plug-flow and complete-mix organic waste digesters rely on the hydraulic retention time (HRT) to control the solids residence time sufficiently to promote methanogenic growth. At mesophilic temperatures, effective treatment dictates that the HRT be maintained at greater than 10 days and, in practice, a 20-40 day HRT is common. The volume of the digester is directly proportional to the chosen HRT and the volumetric rate of waste production. Again, like temperature, the long HRT requirements of these anaerobic digesters dictate that feed waste slurries must have as high a TS content as possible to minimize excess water, which takes up digester volume and results in a higher digester volume requirement to achieve the design HRT.

Currently, when treating manure waste, many livestock facilities use large volumes of water for barn flushing, resulting in excessive amounts of dilute wastewater (<1% TS). This effectively precludes these operations from using conventional plug-flow and complete-mix manure digesters due to both the uneconomical digester volume requirements and the excessive energy required to heat the dilute manure to mesophilic temperatures for effective digestion. Ideally, an anaerobic digestion apparatus for effective treatment of flushed manure should be able to operate at ambient temperatures, tolerate much shorter HRTs, and handle small amounts of fibrous solids.

Fixed-film anaerobic digesters use an internal support media to provide large surface areas for bacterial attachment. Thus, a greater concentration of bacteria is available to mediate the degradation of organic matter. This allows bacterial residence time to be maintained independently of the HRT of the liquid phase. Using much higher concentrations of attached bacteria allows fixed-film digesters to operate at much shorter HRTs and at much lower temperatures while achieving similar treatment efficiencies as conventional plug-flow and complete-mix systems. Currently, designs for high-rate anaerobic processing systems that use fixed-film digesters are available. However, none of the existing fixed-film designs are suitable for wastewaters with significant levels of suspended solids, such as those found in flushed manure. Suspended solids loading for existing fixed-film reactors are limited to less that 10% of the influent chemical oxygen demand (COD).

Livestock manure often includes materials used for bedding, such as hay, sawdust or sand. Often, such materials are poorly degraded or non-biodegradable. Where manure is in liquid form, the liquid is often conveyed into a "lagoon" after separation using solid-liquid separation equipment, with the resultant solids spread on land. Manure presents a complex substrate for anaerobic digestion because the volatile solids content is comprised of readily digestible soluble materials; fine particles that have a high surface-to-volume ratio and are readily accessible to bacterial enzymes; and larger fibrous particles that are relatively inaccessible to microbial attack. These larger fibrous particulates can contribute to clogging of packing material or media. The larger fibrous particulates can also hinder the attachment of bacteria to the media. Ultimately, these situations can lead to short-circuiting of the anaerobic system, which reduces the effectiveness of the biological treatment system. In addition, scum formation is a problem as well as blockage of pipes and other ancillary equipment caused by floating and suspended solids.

For example, certain anaerobic processing systems, such as those disclosed in U.S. Pat. No. 4,183,809, provide for anaerobic microorganisms suspended in a liquid medium to which wastewater is fed. Such processing systems, also known as upflow anaerobic sludge blanket (UASB) reactors, rely on the tendency of anaerobic microorganisms to form flocs or granules (sludge), which are retained within the system by an efficient gas/solids/liquid separation device. Unfortunately, with this system, the microorganisms may be washed out along with the effluent when high levels of particulates are contained in the wastewater. Because of this and the fact that it is difficult to obtain granular sludge with flushed manure, these systems have not been implemented for managing livestock manure.

In other anaerobic processing systems known as fluidized or expanded-bed reactors, the microorganisms are retained within the processing system by attachment to small inert particles (or "packing material"). Suitable particles include sand, anthracite, granular activated carbon, PVC particles, or diatomaceous earth. For example, U.S. Pat. Nos. 3,846,289, 3,956,129, 4,009,099, 4,284,508, and 5,232,585 disclose methods and apparatuses for denitrifying wastewater using solid particulate carriers where particle size generally ranges from about 0.2 to 3 millimeters. Such systems, however, suffer from washout of media and/or reduced media separation efficiency when wastes with suspended solids are treated.

Additional known anaerobic processing systems immobilize the microorganisms on a matrix within the reactor, called fixed-bed reactors. As disclosed in U.S. Pat. Nos. 4,366,059, 4,530,762, 4,561,168, and 4,599,168, the matrix is composed of an inert packing material, or "media," to provide a surface for microorganism attachment and biofilm development. Unlike the fluidized system and the expanded-bed systems described above, the media includes sheet, ring, or spherical material configured in either a random-pack or an oriented arrangement.

Random-pack (or "loose-fill") media include such materials as gravel, wood chips, or special plastic pieces designed with a high "surface to air volume" ratio and are packed in loose-fill configuration in fixed-bed reactors. For example, U.S. Pat. Nos. 4,366,059, 4,780,198, and 5,419,833 disclose random-pack media of plastic rings or cylinders. As with the expanded-bed reactors, the random-pack media have poor hydraulic properties when applied to flushed manure. In particular, random-pack materials tend to clog quickly due to the recalcitrant suspended solids often found in flushed manure (e.g., animal hairs, grain husks, fibrous particles and inorganic precipitates), which causes the wastewater to cease to flow evenly through the media, reducing the effective treatment capacity.

In contrast, oriented (or "ordered") media provide improved hydraulic properties with certain waste products. Known oriented media include materials such as those disclosed in U.S. Pat. Nos. 4,530,762, 4,599,168, 5,228,995, and 6,126,816 for perforated PVC sheets, which are configured in modular blocks with cross-flowing channels located within the blocks. Although current oriented media provide improved hydraulic properties compared to those systems described above, oriented media still tend to suffer from the problem of clogging with respect to aqueous wastes that have significant levels of suspended solids, such as flushed manure. These modular block media promote the settling of suspended particles by decreasing the vertical distance the particles must travel before striking a surface. This promotes accumulation of solids on the media, which impairs biofilm interaction with the wastewater.

Anaerobic digesters with flexible film media and mechanical agitation for flushing/mixing within the system to address the issue of clogging in media have been described (U.S. Pat. Nos. 5,096,579; 6,254,775). These systems are designed for manure with 8-10% TS and are not applicable to flushed livestock waste. Also, these systems operate at a HRT of 28-30 days. Thus, no anaerobic fixed-film bioreactor system currently exists that can effectively treat flushed livestock manure.

BRIEF SUMMARY OF THE INVENTION

The subject invention provides systems and methods for the efficient anaerobic digestion of organic waste. Specifically, the subject invention relates to improvements in various features of anaerobic waste treatment systems and methods, including improved media for anaerobic microorganism attachment and improved digester systems.

Certain embodiments of the subject invention provide improved media for use in an anaerobic digester system, including the digester system of U.S. patent application Ser. No. 10/277,486, filed Oct. 22, 2002. Contemplated anaerobic digester systems of the invention include, but are not limited to, batch and semi-continuous digester processes such as plug-flow digesters, complete mix digesters, and lagoons.

Improved media for retaining anaerobic microorganisms of the invention include, but are not limited to, restrained and unrestrained pliant media and non-pliant media. Pliant media, according to the subject invention, are comprised of media that are capable of readily yielding to force or pressure without breaking (such as cotton, flax, jute, hemp, satin, silk, and sisal). Such pliant media are "restrained" or mounted on racks or frames to afford control over the location of the media within an anaerobic digester.

Unrestrained pliant media, according to the subject invention, are comprised of pliant media that are freely suspended in an anaerobic digester, without the use of frames or other items to control the location of the media within the anaerobic digester.

Non-pliant media, according to the subject invention, are comprised of materials that are incapable of or resistant to bending. Examples of non-pliant materials for use in the manufacture of media of the invention include, but are not limited to, metals, glass, plastics, wood and the like. Non-pliant media may be restrained or unrestrained.

In certain embodiments of the invention, unrestrained, pliant media are provided in a fixed film anaerobic digester system for treating flushed organic waste, wherein the system comprises a closed digester tank that is located above the ground. In another embodiment, restrained pliant media are provided in an above-ground, closed, anaerobic system. In yet another embodiment, restrained, non-pliant media are provided in above-ground, closed anaerobic digester systems. Unrestrained, non-pliant media can also be provided in either above-ground digester systems. Further, any combination of media can be provided in an above-ground digester system (for example, both unrestrained and restrained non-pliant media can be provided together in an above-ground digester).

In a related object of the invention, improved media of the invention are used in a subterranean, anaerobic digestion system. Subterranean, as used herein, refers to items that are wholly beneath or partially located within the ground. Subterranean, anaerobic digestion systems of the invention can be self-contained (such as wholly covered), partially self-contained (such as partially covered), or entirely uncovered.

Certain embodiments of the invention include unrestrained, pliant media in a subterranean anaerobic digester system for treating flushed waste. In other embodiments, restrained pliant media are provided in a subterranean anaerobic system. Further embodiments of the invention provide restrained, non-pliant media and/or unrestrained, non-pliant media in a subterranean, anaerobic digester system.

Accordingly, it is an object of the invention to provide light weight media having substantial surface area for use in above-ground or subterranean anaerobic digester systems.

Another object of the invention is to provide a subterranean anaerobic digester system that includes the improved media of the invention for use in reducing odors associated with the wastewater. A related object of the invention is to provide a unique method for carrying out anaerobic digestion of flushed waste, with special emphasis upon the storage and conservation of methane gas for use as a source of energy.

In addition to minimizing offensive odors and producing usable energy, anaerobic digestion has several other important benefits. One advantage is nearly complete retention in the digester effluent of the fertilizer nutrients (nitrogen, phosphorous, and potassium) that are in the raw manure entering the digester. Organically bound nutrients are mineralized to soluble forms during the anaerobic digestion process—transforming valuable plant nutrients into a more predictable fertilizer product. Also, a broad spectrum of microbial pathogens is destroyed by anaerobic digestion. This may have particular significance for animal health by providing cleaner water for use in recycled flush systems. The potential of the subject fixed-film digester to provide treated wastewater for recycle flushing is especially valuable as water becomes an increasingly precious limited resource.

It is a still further object of the present invention to provide efficient anaerobic digester systems and methods for managing aqueous forms of agricultural waste (such as livestock manure in an aqueous mixture, dead livestock in an aqueous mixture, residual crops in an aqueous mixture), marine and terrestrial biomass, and other bio-organic residues wherein the aqueous mixtures are treated at ambient or higher temperatures to generate a usable biogas.

It is a still further object of the present invention to provide a subterranean anaerobic digester system and method for flushed waste digestion wherein the subterranean system is either a closed or open system. Examples of open, subterranean anaerobic digester systems include those that are uncovered or partially covered. Examples of closed, subterranean anaerobic digester systems include those that are wholly covered.

It is a still further object of the present invention to provide a subterranean anaerobic digester system and method for flushed waste digestion that reduces odors without requiring a cover.

It is a still further object of the present invention to provide a closed, above-ground anaerobic digester system and method for managing organic waste that provides ease of inspection and maintenance of media structure.

It is a still further object of the present invention to provide an improved media for use in available anaerobic digester systems and methods for manure digestion to reduce the levels of pathogens in livestock waste.

It is a still further object of the present invention to provide a closed system apparatus and method for manure digestion to generate solid and liquid fertilizer with increased nutrient availability (i.e. nitrogen and phosphorus).

It is a still further object of the present invention to provide a closed system apparatus and method for manure digestion to generate recycled water for flushing livestock waste or for crop production.

Further objects and advantages of the present invention will become apparent by reference to the following description of the preferred embodiment and appended drawings.

DETAILED DISCLOSURE OF THE INVENTION

Figure 1A:
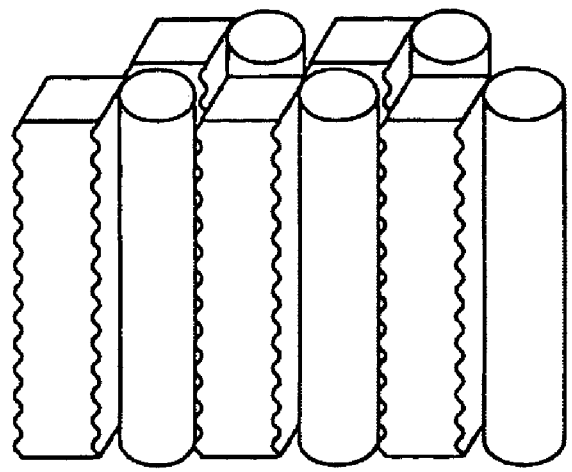
FIGS. 1A-1G are perspective views of an arrangement of vertically-oriented uninterrupted channels of non-pliant media in accordance with the subject invention.

The present invention provides anaerobic digester systems that include restrained or unrestrained, pliant or non-pliant media as structures on which anaerobic microorganisms can attach. As contemplated herein, restrained or unrestrained media can be included in either above-ground closed digester tanks, covered subterranean anaerobic digesters, partially covered subterranean anaerobic digesters, or uncovered subterranean anaerobic digesters. Covered anaerobic digesters are closed systems that include a means for collecting and distributing biogas.

In operation, flushed waste is directed into an anaerobic digester system of the invention, which includes a digester, an influent and effluent line, a feed pump, and media inside the digester, wherein the media is selected from restrained or unrestrained, pliant and non-pliant media. More specifically, the influent line directs flushed waste to the digester via the feed pump and the effluent line removes the treated waste from the digester. In the case of an anaerobic lagoon, the wastewater may be gravity fed, rather than pumped, into the lagoon.

In certain embodiments, a method of operating an anaerobic digester system in accordance with the subject invention includes the step of pretreating the waste to provide suitable flushed waste for efficient and productive anaerobic digestion.

Definitions

Unless otherwise stated, the following terms used in the specification and claims have the meanings given below.

The term "digester", as used herein, refers to above-ground digester systems and subterranean digester systems (including digester tanks).

The term "subterranean," as used herein, refers to location of an anaerobic digester system of the invention, wherein the location is either wholly or partially below the earth's surface.

As used herein, the terms "anaerobic microorganism" and "bacteria" can be used interchangeably and refer to those organisms that anaerobically degrade organic matter.

As used herein, the term "biogas" refers to the gases produced as a result of the anaerobic degradation of flushed waste according to the subject invention. Examples of biogas components include methane ($CH_4$), carbon dioxide ($CO_2$), and hydrogen sulfide ($H_2S$).

As used herein, the term "flushed waste" refers to waste that has been subjected to dilution with water. In certain embodiments, the waste is first pretreated prior to dilution with water. In other embodiments, the waste is first diluted with water and then the flushed waste is subjected to pretreatment prior to introduction to an anaerobic digester of the invention. In one embodiment, livestock manure that has been subjected to dilution with water is pretreated prior to introduction to an anaerobic digester. Often, flushing of livestock waste assists in the transportation and application of the waste. It is also possible to create "flushed livestock manure" from sand separation and washing systems. In an embodiment, flushed livestock waste contains 0-5% suspended solids.

As used herein, the term "livestock" refers to all domesticated animals, including horses, swine, all varieties of cattle such as dairy cows, steer, yak, goats, or any animals whose waste is subject to dilution with water for conveyance or processing.

As used herein, the term "fixed-film media" refers to a support material placed inside a digester of the invention, which provides surface area to promote bacterial attachment and biofilm development.

As used herein, the term "pretreatment" refers to the substantial removal and/or comminution of materials present in organic waste. The materials that can be removed in accordance with the invention include, but are not limited to, inorganic material such as sand, and fibrous materials that are relatively indigestible anaerobically. Methods for removing such materials from waste, i.e., livestock waste, agricultural waste, municipal waste, industrial waste, etc., include, for example, gravity settlement and/or mechanical screening. In certain instances, prior to the step of removing suspended solids and introduction to the fixed-film media of the subject invention, chemical compounds can be added to waste (i.e., livestock waste, municipal waste, industrial waste, etc.) to induce unwanted solids (i.e., fibrous or suspended solids) to flocculate for ease of removal. Methods for comminution include mechanical and/or chemical methods for rendering small the size of suspended solids. Other methods for pretreating waste in accordance with the subject invention include biological/chemical treatment of waste (i.e., hydrolysis of solid waste) or pasteurization of pretreated waste prior to introduction to an anaerobic digester of the invention.

As used herein, the term "sludge" refers to those solids, including biologically inert materials, which remain in the digester after flushed waste has been subjected to anaerobic digestion, in accordance with the present invention. Sludge can also include readily digestible materials and/or fine particles readily accessible to bacterial enzymes that were not fully degraded according to the present invention.

As used herein, the term "treated waste" refers to flushed waste that has been subjected to anaerobic digestion according to the present invention.

As used herein, the term "waste" refers to materials such as livestock waste, municipal waste (i.e., pre-consumer and post-consumer food wastes), industrial waste (i.e., food processing wastes; paper processing wastes), agricultural waste (i.e., crop residues, landscape trimmings, etc.), aquacultural waste, and other marine and terrestrial biomass. As will be apparent to the ordinary skilled artisan in view of this disclosure, the anaerobic digester systems and methods of the subject invention can be applied for treatment of wastes that include, but are not limited to: brewery, distillery, winery, pharmaceutical, cannery, cheese processing, potato processing, pulp and paper, and yeast production.

As used herein, the term "restrained," refers to the permanent arrangement and/or position of media in an anaerobic digester of the invention. For example, restrained pliant media can refer to mesh media that are confined to a specific arrangement within a frame and/or restrained pliant media can refer to the actual permanent position or location of the mesh media within an anaerobic digester of the invention.

The term "unrestrained media," as used herein, refers to the media whose arrangement and/or position within an anaerobic digester is changeable.

As used herein, the term "uninterrupted channels" refers to continuous, unbroken passages through which flushed waste will flow in the direction set by the channels. In contrast, the term "interrupted channels," as used herein, refers to passages intermittently punctuated with apertures that allow flushed waste to flow out of the passage; thus, flushed waste flows through, but not necessarily in the direction set by, the channels.

Fixed-Film Media

According to the subject invention, microbial flora are retained within an anaerobic digester by attachment to media. The media is preferably composed of support materials such as plastics (i.e., polyvinyl chloride, polyethylene, polypropylene, etc.), wood, and metals (i.e., steel, aluminum, etc.). Active biomass (microbial flora) is retained as an attached biofilm on the media, wherein the thickness of the biofilm is controlled by the flow velocity of the flushed waste through the anaerobic digester system.

In certain embodiments, the media of the subject invention are oriented media. The media includes substantially vertically-oriented or horizontally-oriented, uninterrupted channels of roughly 2-6 inches in diameter. For example, thermal plastic pipe (PE, PVC, PP, ABS, etc.) can be employed as the oriented media in the fixed-film digester. The subject media uniquely reduces the likelihood of clogging associated with dilute wastewaters containing significant levels of suspended solids by allowing fine suspended solids to pass freely through the media.

In certain embodiments, the media of the subject invention are corrugated media. Corrugation, according to the subject invention, can run either horizontally or vertically along a channel. Examples of media with horizontal corrugation are illustrated in FIGS. 1A-1G. Examples of commercially available materials (AQUATIC ECO-SYSTEMS, INC.; Apopka, Fla.) having vertical corrugation for use as media in the subject invention are illustrated in FIG. 2.

In one embodiment, the media of the invention includes straight corrugated or non-corrugated vertical tubes having a cross-sectional that is substantially circular or rectangular in shape. In a preferred embodiment, the media include straight corrugated vertical tubes having a cross-sectional area that is substantially circular.

In certain embodiments, the media of the subject invention are arranged in one or more layers. In one embodiment of the invention, all layers of the media are restrained, non-pliant media having vertically-oriented channels that are identical with one another. For example, in all layers of the restrained, non-pliant media, the vertically-oriented, substantially uninterrupted channels are corrugated and have identical cross-sections. In another embodiment, all layers of the media are unrestrained, non-pliant media having vertically-oriented channels that are identical to one another.

The cross sectional diameters of the vertically-oriented channels of the subject invention are preferably between about 1 inch to about 6 inches in diameter. In a related embodiment, all layers of the fixed-film media are composed of vertically-oriented, wholly corrugated channels having a circular cross-section of about 2-6 inches in diameter. In another embodiment, all layers of the fixed-film media are composed of vertically oriented, wholly non-corrugated (straight) channels having a circular cross-section of about 2-6 inches in diameter.

A given layer of restrained and/or unrestrained non-pliant media can be wholly corrugated, wholly non-corrugated, or contain a mixture of corrugated and non-corrugated media. Multiple layers may include any combination of wholly corrugated media layers, wholly non-corrugated media layers, or a mixture of the two types of media within layers. The diameter and/or shape of the cross section of media can vary between layers or within layers, i.e. different sizes from one layer to the next or different diameter sizes within a layer.

Any combination of the above (i.e., wholly corrugated, wholly non-corrugated, different shaped cross-sections, a mixture of corrugated and non-corrugated, different sized diameters) can be provided either in a random or deliberate fashion, either within a layer or between layers.

Figure 2:
FIG. 2 is a perspective view of a commercially available material used to create a vertically-oriented channel of non-pliant media with vertical corrugation.

In one embodiment, as illustrated in FIG. 1A, corrugated and non-corrugated channels having different cross-sectional shapes (i.e., corrugated channels have circular cross sections and straight channels have square cross sections) are intermingled in at least one single layer of the fixed-film media of the invention.

Figure 1B:
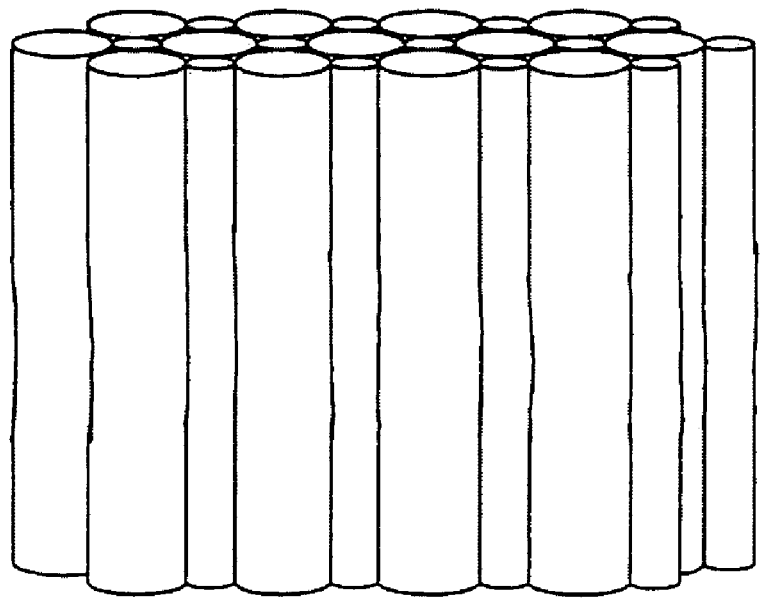

In another embodiment, as illustrated FIG. 1B, non-corrugated channels having different cross-sectional diameters are intermingled in at least one single layer of the fixed-film media of the invention.

Figure 1C:
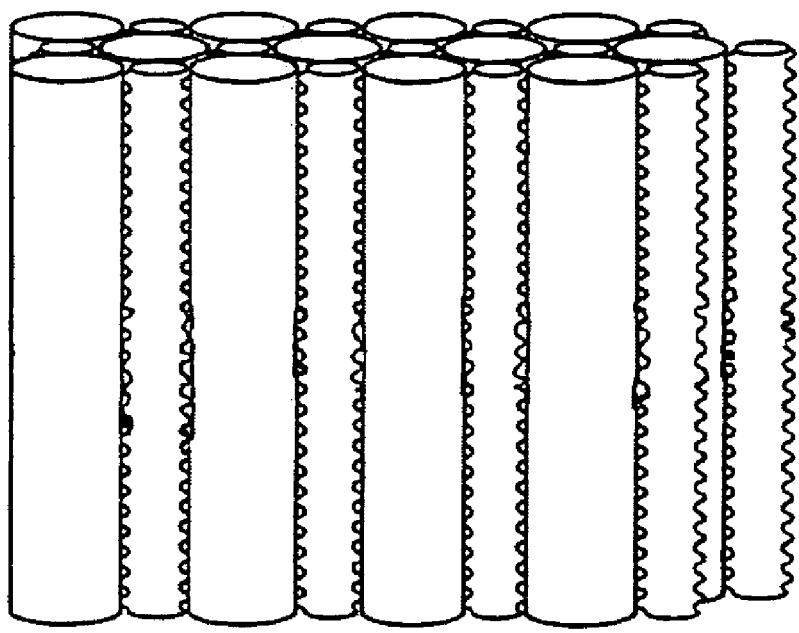

In another embodiment, as illustrated in FIG. 1C, both corrugated and non-corrugated vertically-oriented channels having different diameters but similar cross-sectional shapes (i.e., circular cross section of one form of media is 3-4 inches in diameter and another form of media is 1-3 inches in diameter having a circular cross section) are intermingled to form at least one layer of the fixed-film media for use in a digester tank of the invention. The corrugated channels can be randomly intermingled with the non-corrugated channels or both corrugated and non-corrugated channels can be assembled in an ordered fashion to form at least one layer of the fixed-film media of the invention.

Figure 1D:
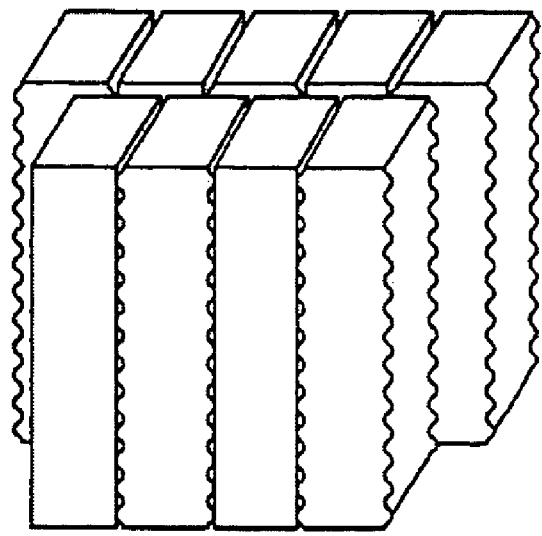
Figure 1E:
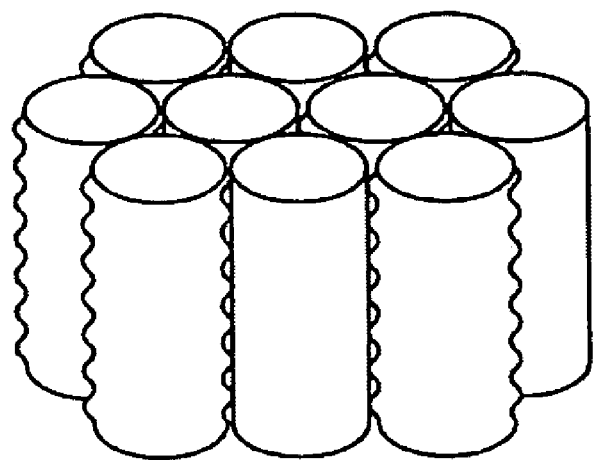

In certain embodiments, as illustrated in FIGS. 1D-1E, corrugated and non-corrugated channels having the same cross-sectional shape and substantially the same diameter (i.e., FIG. 1E illustrates a media layer comprising corrugated and non-corrugated channels have circular cross-sections with substantially similar diameters) are intermingled to form at least one layer of a fixed-film media of the invention.

Figure 1F:
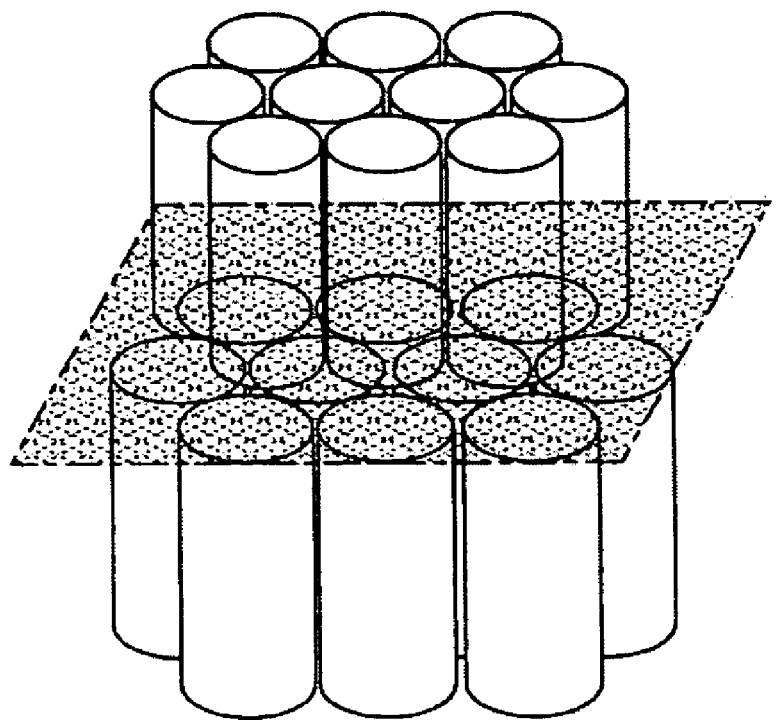

In yet another embodiment, as illustrated in FIG. 1F, channels characterized by a first diameter are situated within a single first layer of the fixed-film media and channels characterized by a second diameter are situated within a single second layer that is located beneath the first layer of media. In preferred embodiments, any combination of channels with diameters between 1 to 6 inches can be provided altogether in a single layer of the fixed-film media. For example, in a layer of the fixed-film media, at least one substantially vertically-oriented, uninterrupted channel is provided having a 2 inch diameter and at least one other substantially-vertically-oriented, uninterrupted channel is provided that has a 3 inch diameter. Alternatively, any combination of channels with diameters between 1 to 6 inches in diameter can be provided separately in different layers of the fixed-film media. For example, the vertically-oriented uninterrupted channels in a first layer of the fixed-film media are of identical diameters between 1 to 6 inches and vertically-oriented uninterrupted channels in a second layer of the fixed-film media are of identical diameters between 1 to 6 inches that are different from the diameters of the channels of the first layer.

Figure 1G:
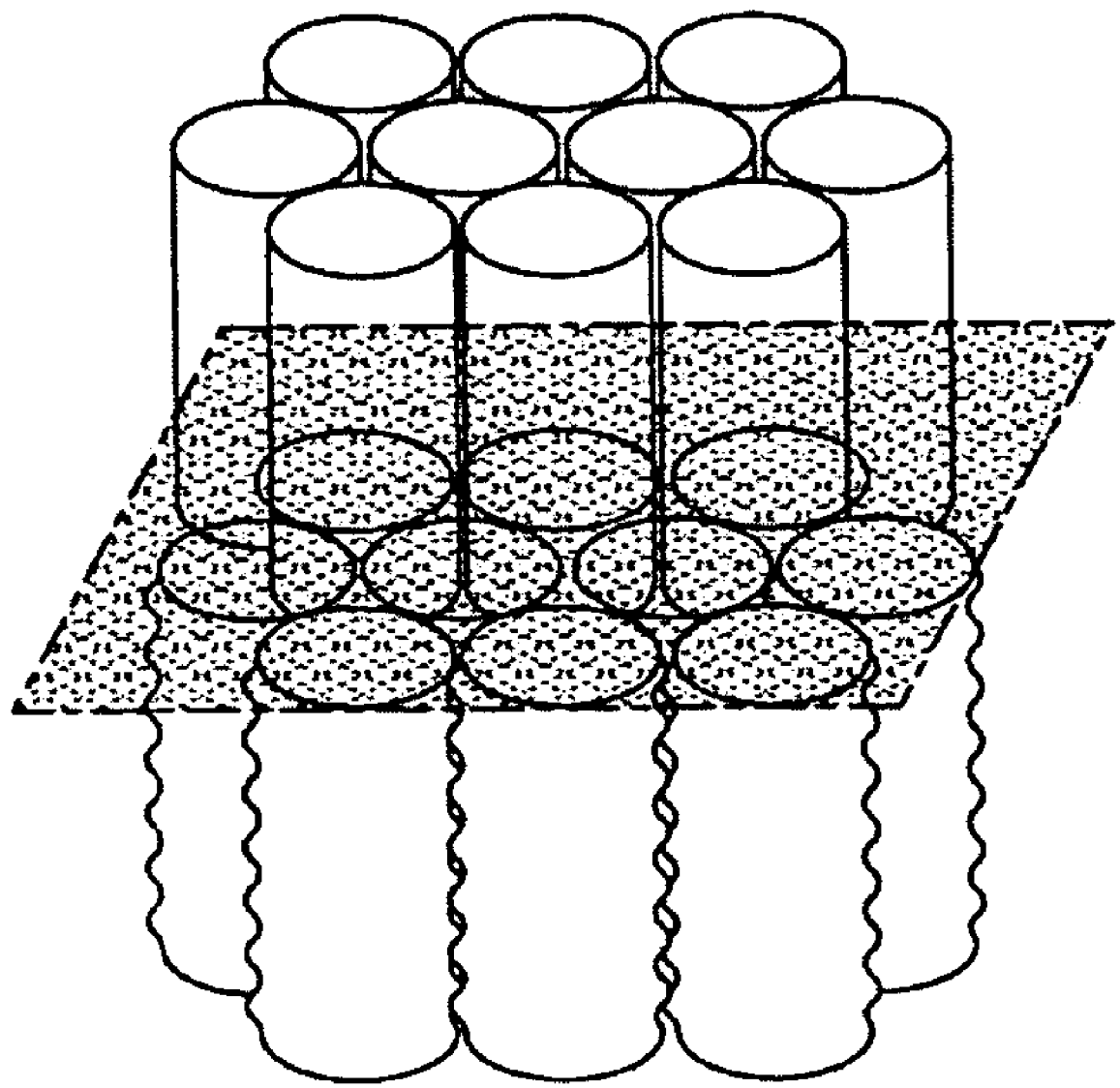

Alternatively, as illustrated in FIG. 1G at least one layer of the fixed-film media is composed wholly of corrugated vertically-oriented channels and at least one other layer of the fixed-film media is composed wholly of non-corrugated vertically-oriented channels.

Figure 3:
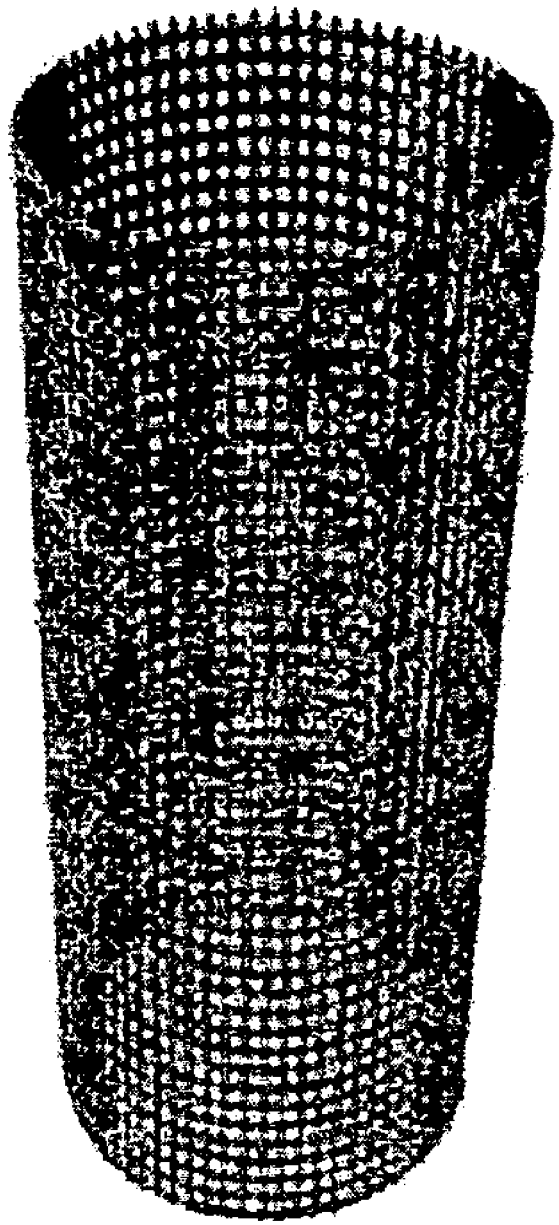
FIG. 3 is a perspective view of a commercially available material used to create a vertically-oriented interrupted channel of non-pliant media in accordance with the subject invention.
Figure 4A:
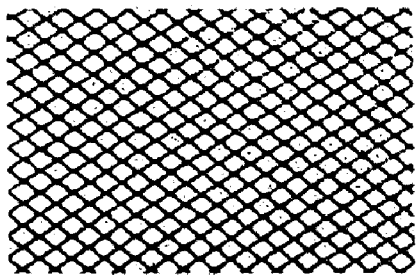
FIGS. 4A-4D are illustrations of various commercially-available mesh materials for use as media in the subject invention.
Figure 4B:
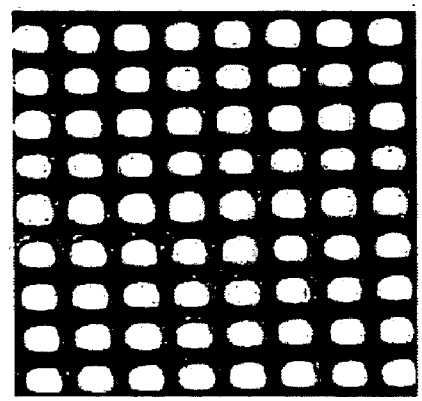
Figure 4C:
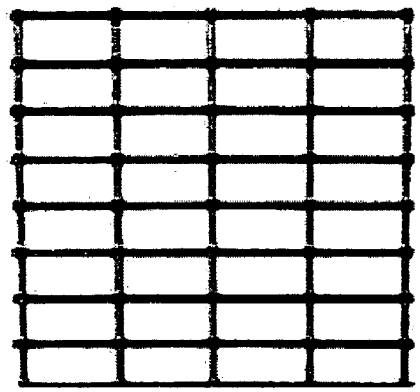
Figure 4D:
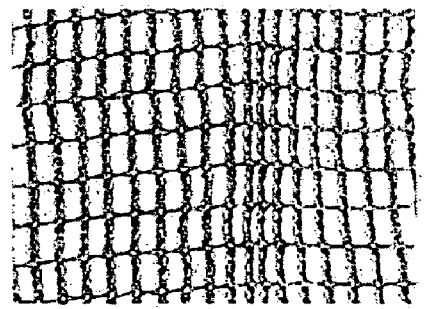

In certain embodiments, restrained, non-pliant media of the invention are composed of vertically-oriented, interrupted channels. FIG. 3 illustrates an example of a commercially available material (AQUATIC ECO-SYSTEMS, INC.; Apopka, Fla.) that can be used as a vertically-oriented interrupted media of the invention. As illustrated in FIG. 3, a media channel can be perforated or "interrupted" in accordance with the subject invention.

The subject invention also provides improved media for use in an anaerobic digester system, including above-ground anaerobic digester systems and subterranean (such as wholly beneath the ground or partially within the ground) digester systems. The improved media of the invention include restrained or unrestrained, pliant or non-pliant media.

In accordance with the subject invention, pliant mesh media can be provided in anaerobic digester systems, onto which anaerobic microorganisms are retained. Various forms of pliant mesh, such as those examples illustrated in FIGS. 4A-4D, as provided by AQUATIC ECO-SYSTEMS, INC.; Apopka, Fla., can be composed of any durable material including cloth (such as cotton, flax, jute, hemp, satin, silk, sisal, etc.), nylons, polyesters, rayon, other polymeric materials, and plastics (such as polyvinyl chloride, polyvinyledine chloride, polypropylene, polyethylene, etc.), wherein the mesh of the invention comprises a plurality of apertures to increase surface area for a greater number of microorganism adherence.

In one embodiment, pliant mesh media are provided in an anaerobic digester in accordance with the subject invention. The restrained, pliant mesh media of the subject invention can be composed of materials with reinforced edges having sufficient tensile strength and/or buoyancy to allow the media to hang vertically within liquid in an anaerobic digester.

Figure 5:
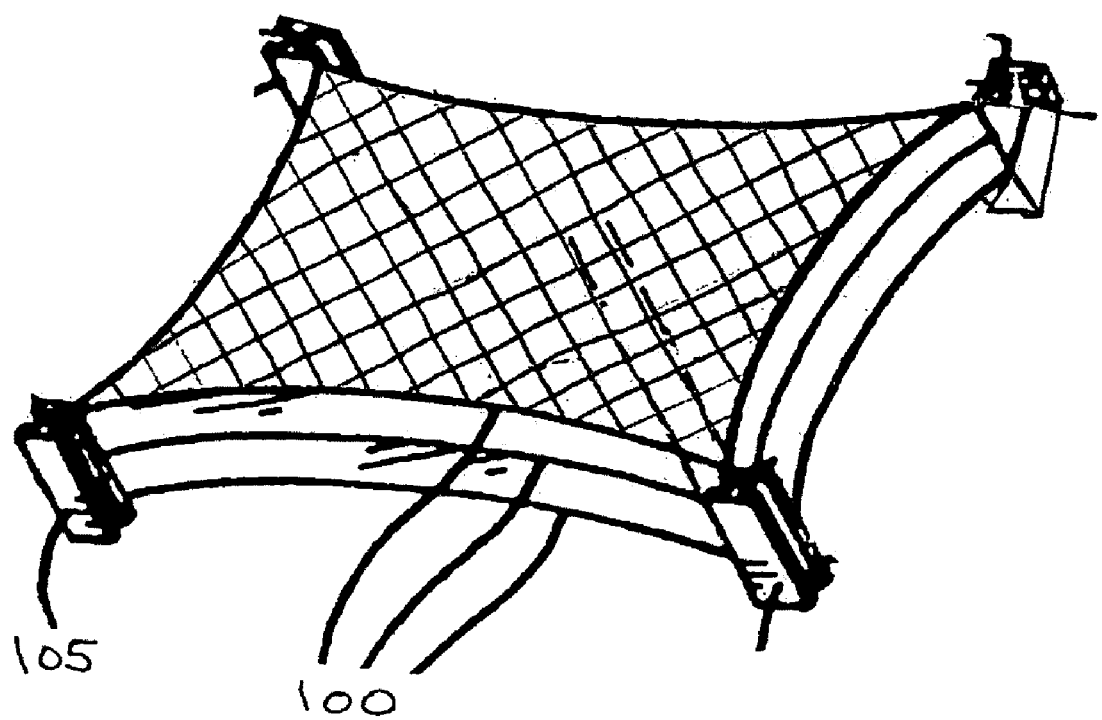
FIG. 5 is a perspective view of an embodiment of the invention wherein restrained, pliant mesh media are provided for retaining microorganisms.

Alternatively, restrained, pliant mesh media of the subject invention can be attached to a structure that controls the location and/or arrangement of the pliant, mesh media within an anaerobic digester. One embodiment of restrained, pliant mesh media is illustrated in FIG. 5. The pliant, mesh media can be provided in panels 100 that are placed vertically in a frame 105 to control the location and position of the pliant media within an anaerobic digester. The panels can be either a continuous panel (i.e., sheet) or an interrupted panel (i.e., mesh).

The structure that controls the location and position of the pliant, mesh media can be placed in any orientation and/or region of an anaerobic digester. For example, where the pliant mesh media has sufficient tensile strength and buoyancy to allow the media to be vertically-oriented within liquid, the structure to which the mesh media is attached may be placed near or at the bottom of an anaerobic digester. Alternatively, where the pliant mesh media is weighted, a frame to which the mesh media is attached may be provided near or at the top of an anaerobic digester.

In another embodiment, pliant cord or strip media are provided in an anaerobic digester in accordance with the subject invention. Unlike the pliant mesh media, which are generally provided as panels, pliant cord or strip media are long and ropelike in bodily structure. Cord media of the subject invention are preferably composed of twisted strands of durable material. The strands may be composed of the same material or different materials to form a pliant cord media of the invention. In contrast, strip media of the subject invention are composed of long narrow pieces of durable material, usually of uniform width.

Pliant cord or strip media can be composed of any durable material including cloth (such as cotton, satin, silk, etc.), nylons, other polymeric materials, and plastics (such as polyvinyl chloride, polyvinyledine chloride, polypropylene, polyethylene, etc.), wherein the pliant cord or strip media are hung vertically within an anaerobic digester. Pliant cord or strip media are particularly advantageous in anaerobic digesters in that they have no packing interfaces to accumulate solids.

Unrestrained, pliant cord or strip media of the subject invention can be can be composed of materials having sufficient tensile strength and/or buoyancy to allow the media to float within liquid in an anaerobic digester.

Figure 6A:
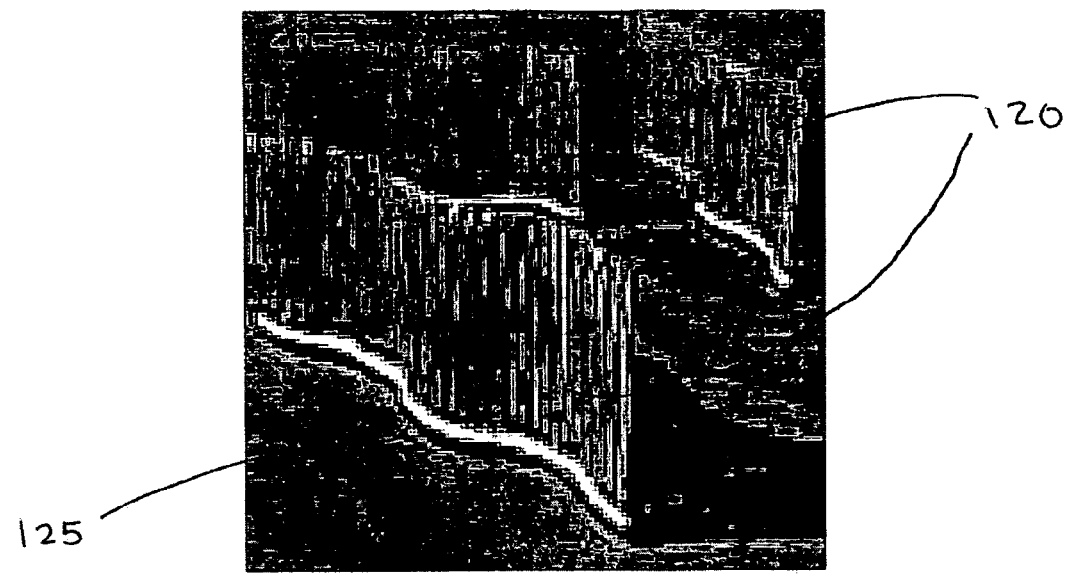
FIGS. 6A and 6B are perspective views of certain embodiments of the invention wherein restrained, cord pliant media are provided for retaining microorganisms.
Figure 6B:
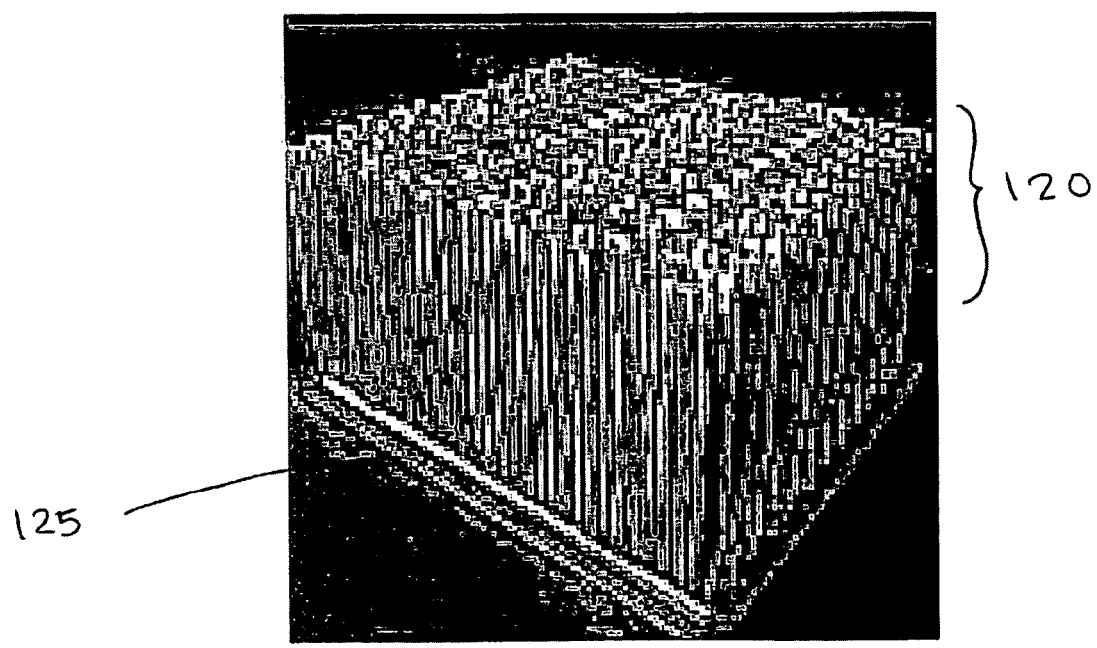

In one embodiment of the subject invention, restrained, pliant cord media are illustrated in FIGS. 6A and 6B. Restrained, pliant cord or strip media 120 of the subject invention can be attached to a structure 125 that controls the location and position of the pliant, mesh media within an anaerobic digester.

The location controlling structure can be provided in any region of the anaerobic digester. For example, in certain embodiments, where the pliant cord or strip media are buoyant, the location controlling structure to which the cord or strip media are attached may be placed near or at the bottom of an anaerobic digester. Alternatively, where the pliant cord or strip media are dense and non-buoyant, the location controlling structure to which the pliant cord or strip media are attached may be placed near or at the top of an anaerobic digester.

Anaerobic Digesters

Anaerobic digesters of the subject invention employ various types of structures. A number of patents that describe anaerobic digester technology include the following: U.S. Pat. Nos. 6,383,371; 6,299,774; 6,291,232; 6,254,775; 6,126,816; 6,096,214; 5,587,080; 5,560,819; 5,518,620; 5,505,848; 5,500,112; 5,419,833; 5,389,248; 5,232,585; 5,228,995; 5,212,090; 5,205,935; 4,672,691; 4,599,168; 4,561,974; 4,366,059; 4,284,508; 4,183,809; 4,026,082; 4,009,099; and 3,933,628.

Certain embodiments of the invention use anaerobic digesters that provide horizontal fluid flow through a trough, labyrinthine, vaned, or bed-like structure are described in the following U.S. Pat. Nos. 4,274,838; 4,334,997; 4,551,243; 4885,094; 5,096,579; 5,403,742; and 5,525,229.

Other embodiments of the subject invention use anaerobic digesters that have multi-stage component digester vessels. Examples of such anaerobic digesters are disclosed in U.S. Pat. Nos. 4,318,993 and 5,500,123.

Further embodiments of the subject invention use anaerobic digester systems that use a columnar or vertical vessel with trickle-down fluid flow through horizontal bed layers. U.S. Pat. Nos. 5,413,713 and 5,618,412 provide descriptions of such digesters.

Yet other embodiments of the invention use anaerobic digester vessels that include a vortex fluid flow. Such digesters are disclosed in U.S. Pat. No. 5,499,770.

In one embodiment of the invention, the anaerobic digester system of the invention includes a digester tank that is located above the ground or partially or wholly underneath the ground, within which media of the invention is situated. The digester tank can include an influent line for introducing flushed waste to the tank and an effluent line for removing treated waste from the digester tank. The effluent line can exit from either the lower or upper zone of the tank. A portion of the treated livestock waste can also be recycled back into the influent line to promote more uniform biofilm development and activity.

A further embodiment provides a means for re-circulating settled solids back into the tank to provide an agitation means for preventing the "bridging" of accumulated solids within the lower region of the tank. "Bridging" refers to the solidified sludge formed as a result of settling and interweaving of large particulates. The gases generated by the anaerobic digestion of the livestock waste are captured and removed at the upper portion of the tank. These gases can be flared to burn off the excess methane or used to produce energy, such as heat or electricity.

With a completely closed system, an anaerobic digester system of the invention allows for the thorough anaerobic digestion and conversion of odorous organic intermediates found in stored wastewater into less offensive compounds. The composition and concentration of bacterial groups in the biofilm developed on the media in the subject invention result in a significantly enhanced anaerobic degradation process. Further, the subject invention provides an anaerobic digester that functions effectively at ambient temperatures and short HRTs. A closed, anaerobic digester system of the invention can be located either above ground or be a subterranean digester system.

Another embodiment of the subject invention includes a digester tank (located subterranean or above-ground) with a conical-shaped bottom. The conical bottom serves to accumulate suspended solids and provides access space for inspection and maintenance below the media. The conical-shaped bottom collects any sludge at the apex of the bottom. The collected sludge can be recycled using a recycle pump and line into the influent line. Alternatively, the collected sludge can be removed and applied to land as fertilizer.

The digester system according to the present invention includes an access hatch that provides ease of inspection and maintenance below the media.

The system typically produces biogas at 80-90% methane ($CH_4$) and 10-20% carbon dioxide ($CO_2$), depending on organic loading rate, temperature and HRT. For every kilogram of chemical oxygen demand (COD) of waste converted by the process, 0.35 $m^3$ of $CH_4$ (dry gas at 0° C. and 1 atm) is produced. The biogas produced from the digester can be flared to further reduce odors and emissions of methane, a potent greenhouse gas. Potential options for biogas utilization include use as a fuel to produce heat, electricity, or motive force (for example: production of hot water; generation of electricity for on-farm use; refrigeration (i.e., absorption, adsorption, compression, or crystallization cooling methods); and vehicular fuel).

In another embodiment of the invention, the anaerobic digester is a conventional lagoon or waste storage pond. As contemplated herein, the lagoon or pond can be naturally occurring or man-made. In certain embodiments, the lagoon or pond is created with materials (i.e., concrete "pool") that prevent escape of flushed waste from the anaerobic digester.

For example, the lagoon or waste storage pond of the invention can include a non-corrosive, high-density polyethylene skin to form a basin to which flushed waste is introduced. Such a skin will prevent leaking and/or pollution problems with groundwater, rivers, lakes, and coastal waters.

A lagoon or waste storage pond subterranean anaerobic digester of the invention can include an influent line for introducing flushed waste to the digester and an effluent line for removing treated waste from the digester. The effluent line can exit from either the lower or upper zone of the digester. A portion of the treated waste can also be recycled back into the influent line to promote more uniform biofilm development and activity. Such digesters can further include a means for collecting any sludge at the bottom (such as sludge provided through gravity settling) and a means for recycling (such as a recycle pump and line) collected sludge into the influent line. Alternatively, the collected sludge can be removed and applied to land as fertilizer.

Figure 7:
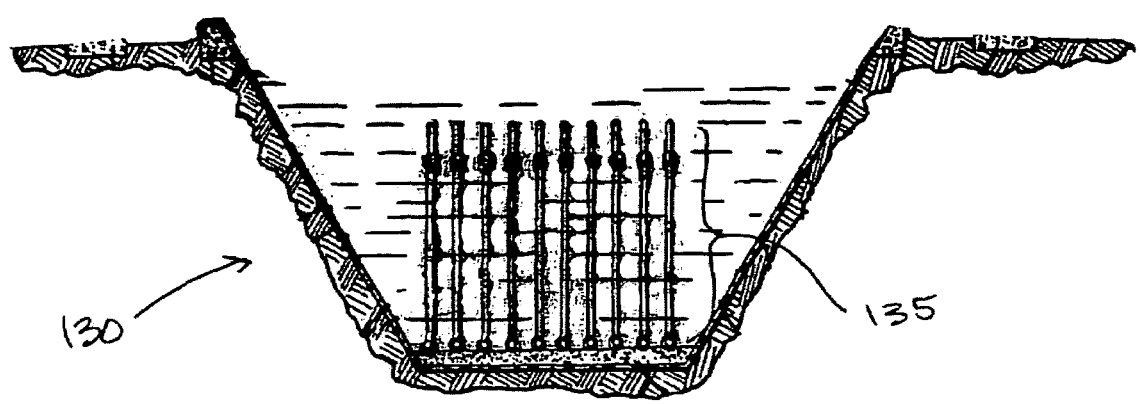
FIG. 7 is a perspective view of a subterranean anaerobic digester system comprising restrained pliant media.
Figure 8:
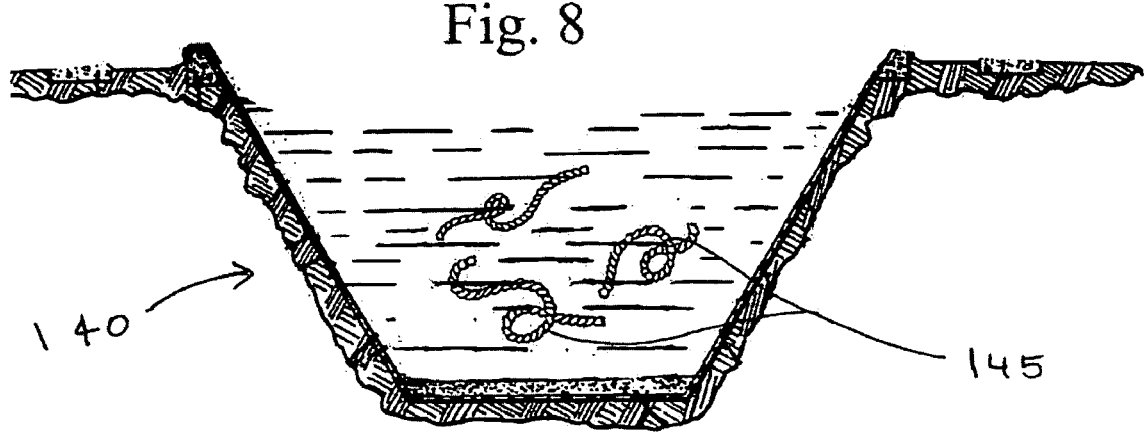
FIG. 8 is a perspective view of a subterranean anaerobic digester system comprising unrestrained pliant media.

As illustrated in FIG. 7, a lagoon-style anaerobic digester is provided 130 that includes restrained pliant cord media 135 for use in retaining anaerobic microorganisms. FIG. 8 illustrates a subterranean anaerobic digester having unrestrained pliant cord media for use in retaining anaerobic microorganisms.

Any of the subterranean anaerobic digesters of the invention can be covered to enable harvesting of biogas released during waste treatment. For example, although not necessary for anaerobic digestion, a lagoon or pond can be covered to collect methane emitted as a result of anaerobic digestion. As with the digester tank, the collected biogas can be flared to further reduce odors and emissions of methane. Alternatively, collected biogas can be used as a fuel to produce heat, electricity, or motive force (for example: production of hot water; generation of electricity for on-farm use; refrigeration (i.e., absorption, adsorption, compression, or crystallization cooling methods); and vehicular fuel).

An influent line directs either flushed waste or pretreated flushed waste to the lagoon or waste storage pond, which includes media of the invention. The effluent line removes the treated waste from the lagoon or pond. In an embodiment, the effluent line removes the treated waste and recycles a portion of the treated waste back into the influent line through a recycle pump or via gravitation force.

Capital costs are one impediment to the implementation of current anaerobic digestion technologies to treat flushed manure. In particular, media used in fixed-film anaerobic digesters can be a significant portion of the cost in constructing these systems. Thus, the selection of media of the subject invention, which is widely available and relatively low in cost, is preferred for reducing economic barriers to the implementation of this technology.

In one embodiment, the media in an anaerobic digester are raised on a support structure. This provides space below the media for accumulation and removal of recalcitrant suspended solids. This eliminates the potential for clogging and short-circuiting and at the same time allows for inspection and maintenance below the media via the access hatch. The media, which can be buoyant, can also be secured by a media support structure positioned above the media.

Fixed-film digesters are ideally suited for treating large volumes of dilute wastewaters, such as those generated by dairy and swine operations, because large numbers of bacteria can be concentrated inside smaller digesters operating at shorter hydraulic retention times than would be needed to achieve the same degree of treatment with conventional suspended-growth anaerobic reactors and covered anaerobic lagoons. Further, fixed-film digesters have a smaller footprint—an important factor where land availability is limited. Also, from an aesthetic perspective, a compact digester design is preferable to large lagoons.

In a preferred embodiment, the fixed-film anaerobic digestion system according to the present invention includes a closed digester tank, a biogas collection system, an influent and effluent line and feed pump, and media inside the tank providing substantially vertically-oriented, uninterrupted channels of roughly 2-6 inches in diameter. The subject digestion system can advantageously treat flushed livestock manure at ambient temperatures while producing a source of energy. Further, the digestion system provides effective treatment of livestock waste at reasonable hydraulic retention times while effectively reducing pathogen levels as well as odors in the treated waste.

An anaerobic digester of the invention is an above-ground digester tank. In the digester tank, immobilization of bacteria as a biofilm on non-pliant or pliant media serves to prevent washout of slower growing cells and provide biomass retention independent of hydraulic retention time. Because more bacteria are available for a given reactor volume as compared to conventional suspended-growth designs and covered anaerobic lagoons used to treat livestock waste, less time is needed to degrade the flushed livestock waste, allowing operation at short hydraulic retention times typically in the range of 2-6 days.

Further, the subject media immobilizes the microbial biomass within the digester tank to allow effective treatment of the flushed livestock waste at ambient temperatures. The temperature of the flushed manure influences the organic loading rate applied to the digester. Table I gives a range of recommended organic loading rates over a range of temperatures. As understood by the skilled artisan, the temperature of the flushed manure can be higher than 35° C. The high loading rates serve to maximize biogas production while the lower loading rates maximize treatment efficiency.

TABLE I

Recommended organic loading rates based on manure wastewater temperatures.

| Wastewater temperature ° C. | Recommended organic loading rates | |
| --- | --- | --- |
| | Low g COD/L/d | High g COD/L/d |
| 15 | 0.2 | 1 |
| 20 | 0.5 | 3 |
| 25 | 1 | 4 |
| 30 | 1.5 | 6 |
| 35 | 2 | 8 |

The influent line directs either flushed livestock waste or pretreated flushed livestock waste to the digester tank. The influent line can provide flushed livestock waste to the digester tank at either an upper or a lower region in the tank. In a preferred embodiment, the influent line provides flushed livestock waste to the lower region of the tank to supply an upflow system. In another embodiment, the influent line provides flushed livestock waste to the upper region of the digester tank to present a downflow system.

The effluent line removes the treated waste from the digester tank. In an embodiment, the effluent line removes the treated waste and recycles a portion of the treated waste back into the influent line through a recycle pump.

In a related embodiment, the excess treated waste is conveyed to subterranean anaerobic digester (i.e., a storage pond or lagoon). Alternatively, excess treated waste can be conveyed to an above-ground storage unit (i.e., silo). Further embodiments contemplate introducing excess treated waste to a CSTR.

By recycling the treated waste, the frequency of contact between the bacterial cells and the media in the fixed-film digester is increased, thereby creating an environment conducive to more uniform biofilm development and activity. This is significant when diffusion of substrates and nutrients into a biofilm is considered. Faster biofilm development allows for quicker commissioning of the reactor by reducing the time taken for the start-up phase. Also, treatment of the wastewater is more rapid due to faster uptake of substrates through a more evenly distributed biofilm.

Pretreatment

In certain embodiments of the invention, flushed waste or solid waste is pre-treated prior to introduction to media of the invention. Pre-treatment can include substantial removal of materials using, for example, gravity settlement and/or mechanical screening. Alternatively, pre-treatment can include comminution methods either alone or in combination with methods for removal of materials.

Pretreatment, according to the subject invention, can also include anaerobic and/or aerobic digestion of the waste prior to introduction to a fixed film media of the invention. For example, pretreatment of flushed livestock waste can include any one or a combination of the following: covered anaerobic lagoon, uncovered anaerobic lagoon, batch digester, plug-flow digester, completely stirred tank reactor (CSTR), upflow anaerobic sludge blanket, and anaerobic sequencing batch reactor (ASBR).

In certain embodiments, pretreatment of flushed waste or solid waste includes the addition of chemical compounds that can effectively break down the waste products into a form that is easily digestible by anaerobic microorganisms. In other embodiments of the invention, flushed waste or solid waste are subjected to biological processes (i.e., enzymatic degradation) that break down the waste products into a form that is easily digestible by anaerobic microorganisms.

In accordance with the present invention, one or more pretreatment methods can be applied to waste. For example, with livestock waste, one ore more pretreatment methods can be implemented prior to, during, or after dilution with water to provide appropriate flushed livestock waste for introduction to a fixed film media of the invention.

In one embodiment, flushed livestock waste is pretreated with both comminution and removal methods. For example, the flushed livestock waste is subjected to comminution via exposure to sodium hydroxide (which causes insoluble fibers to swell) and mechanical maceration of the fibers. Once the fibers are of a desired size, they are subjected to chemical compounds that cause them to flocculate. The waste is then introduced to mechanical separation and/or gravity settling methods to remove the suspended solids. In other embodiments, flushed livestock waste is pretreated with either comminution or removal methods.

According to the present invention, the pretreated flushed waste provides a suitable substrate for efficient and productive anaerobic digestion. In a preferred embodiment, the pretreated livestock waste is dairy manure containing less than 1% suspended solids or biologically inert materials. The subject invention can also be used to treat the filtrate/product of any process or combination of processes that render livestock manure to contain 0-5% suspended solids.

Following is an example that illustrates procedures for practicing the invention. This example should not be construed as limiting. All percentages are by weight and all solvent mixture proportions are by volume unless otherwise noted.

EXAMPLE 1

Figure 9:
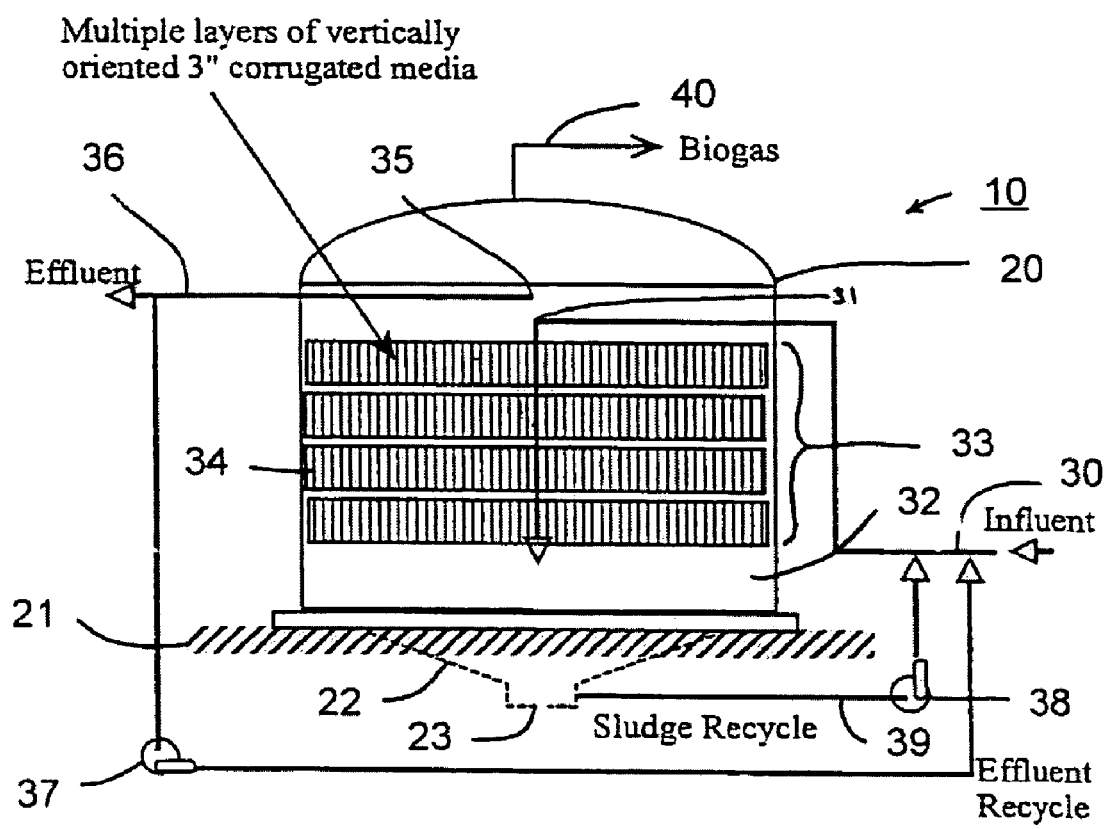
FIG. 9 is a perspective view of an apparatus according to the present invention illustrating the cycle of the system.

Referring now to FIG. 9, a preferred embodiment of a fixed-film anaerobic digester for treatment of flushed livestock manure is illustrated and generally designated by the reference numeral 10. The basic fixed-film digester design 10 consists of a tank 20 filled with plastic media 34 on which a consortium of bacteria (not shown) attach and grow as a slime layer or biofilm (not shown). The closed digester tank 20 consists of a cylindrical (approximately 1:1 height to diameter), glass-lined bolted-steel tank, but can be constructed of other suitable materials and in other shapes, as commonly understood by those skilled in the art.

The media 34 in the fixed-film digester is preferably constructed of vertically arranged, 3 in. diameter, corrugated polyethylene drainage pipe, similar to that commonly used in septic tank drain fields. The media is preferably installed in four layers of 4 ft. pipe 33 and occupies approximately ⅔ of the tank height. In practice, the media can be configured in single or multiple layers, and pipe sizes and composition can be modified as desired for the particular project. Polyethylene pipe is a widely available, light-weight material, which offers a low-cost solution to providing sufficient surface area in the digester for microbial attachment and biofilm development, and is not prone to clogging. With modular and random-pack media, there are multiple points throughout the media-bed where fibrous manure solids can accumulate, whereas only the bottom and top edges of the subject pipe media can accumulate fibers.

Table II lists some preferred properties of the media and the tank. Alternatively, the digester tank can be any size and shape appropriate for the efficient treatment of flushed livestock waste, as commonly understood by those skilled in the art. Also, the closed gas-tight tank can have either a fixed or a flexible roof.

TABLE II

| Example Tank and Media Properties | | |
| --- | --- | --- |
| Tank type | bolted glass fused to steel | cylindrical |
| Tank height | ft | 25.7 |
| Tank diameter | ft | 25 |
| Total volume | $m^3$ | 408 |
| Active liquid volume | $m^3$ | 369 |
| Media volume | $m^3$ | 225 |
| Tank aspect ratio | height/width | 1.03 |
| Media height to tank height | height/height | 0.62 |
| Media polymer | 3" corrugated plastic pipe | polyethylene |
| Media density | $kg/m^3$ | 954 |
| Media porosity | $L/L_m$ | 0.978 |
| Active specific surface area | $m^2/m^3$ media volume | 74 |
| Influent area dispersion | $m^2$/inlet | 46 |

The digester tank 20 is set on a custom-designed slab 21 that preferably has a conical bottom 22 for easy removal or recycling of sludge.

Following pretreatment by mechanical screening and/or gravity settling, the influent wastewater is pumped through the influent line 30 from a sump (not shown). The influent line 30 runs through the wall of the tank 20. The wastewater flows down through the influent line 31 into the holding area 32 below the media zones 33. The wastewater then travels up through the media zones 33.

The treated wastewater flows out of the effluent line 35-36. A portion of the effluent is recycled through a pump 37 back to the influent line 30. Normally, a 3:1 recycling ratio assures even concentrations across the media and even growth of the biofilm. The digested effluent flows to a storage pond (not shown) to be land applied in accordance with a nutrient management plan. A desludging pump 38 removes sludge via the sludge recycle line 39 leading from the apex of the conical bottom 23 and recycles it back into the influent line 30. In an alternate embodiment, some of the sludge can be recycled directly back into the conical bottom to provide an additional means for preventing the "bridging" of accumulated solids within the lower region of the tank.

Biogas leaves the upper region of the digester tank 40 and passes through a sediment trap (not shown) to a mass flow meter (not shown), prior to flowing through a pressure regulator (not shown) and on to the flare (not shown). Both pressure and vacuum emergency relief valves (not shown) are located on the upper region of the tank 20. The biogas produced can be collected and used, for example, either directly (e.g., for heating water) or in an engine generator to provide electricity. The tank also has several sampling ports (not shown) for obtaining mixed liquor samples at various radii from above, below, and within each media zone 33.

Table III gives some sample characteristics of flushed dairy manure before and after pretreatment as found during demonstration of the apparatus.

TABLE III

Example flushed dairy manure characteristics

| Parameter | Units | Concentration |
|---|---|---|
| Before separation | | |
| TS | mg/L | 9837 |
| VS | mg/L | 9722 |
| CODt | mg/L | 9745 |
| After mechanical separation and sedimentation | | |
| TS | mg/L | 5243 |
| VS | mg/L | 3850 |
| TSS | mg/L | 2806 |
| CODt | mg/L | 5613 |
| CODs | mg/L | 1900 |
| PH | pH units | 7.45 |

Table IV illustrates sample operating conditions of an apparatus in accordance with the subject invention for three different conditions.

TABLE IV

Example of three operating conditions for flushed dairy manure digestion

| Parameter | I | II | III |
|---|---|---|---|
| Temperature (° C.) | 29 | 29 | 18 |
| HRT (d) | 3 | 2 | 3 |
| Influent COD (mg/L) | 4609 | 4819 | 5613 |
| Influent soluble COD (mg/L) | 1924 | 2310 | 1900 |
| Organic loading rate (g COD/L/d) | 1.54 | 2.41 | 1.87 |
| COD reduction (%) | 48 | 44 | 40 |
| Soluble COD reduction (%) | 69 | 62 | 49 |
| CH$_4$ Production Rate (L/L$_T$/d @ STP) | 0.26 | 0.37 | 0.26 |

Inasmuch as the preceding disclosure presents the preferred embodiment devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

I claim:

1. A fixed-film anaerobic system for treating flushed waste comprising:
    a) a digester having a floor and an upper and a lower region;
    b) more than one layer of non-pliant media supported within the digester, wherein said layers consist of at least one layer of media of substantially vertically-oriented channels having a first diameter and a first cross-section, and at least another layer of media of substantially vertically-oriented channels having a second diameter and a second cross-section, wherein the second diameter is different from that of the first diameter, wherein at least one layer of the media consists of non-corrugated channels and at least another layer of the media consists of corrugated channels, and wherein said media immobilizes anaerobic microorganisms;
    c) an influent line to direct the flushed waste into the digester; and
    d) an effluent line to remove treated flushed waste from the digester.

2. The system according to claim 1, wherein the layer(s) of media comprising non-corrugated channels and the layer(s) of media comprising corrugated channels are supported in the digester in an ordered fashion.

3. The system according to claim 1, wherein the layer(s) of media comprising non-corrugated channels and the layer(s) of media comprising corrugated channels are supported in the digester in a random fashion.

4. The system according to claim 1, wherein the first cross-section of the at least one layer of media is different from the second cross-section of the at least another layer of media.

5. The system according to claim 4, wherein the layer(s) of media comprising the first cross-section and the layer(s) of media comprising the second cross-section are supported in the digester in an ordered fashion.

6. The system according to claim 4, wherein the layer(s) of media comprising the first cross-section and the layer(s) of media comprising the second cross-section are supported in the digester in a random fashion.

7. The system according to claim 4, wherein the first cross-section is a circle and wherein the second cross-section is a square.

8. The system according to claim 1, wherein said at least one layer of the media comprises at least two different cross-section channels.

9. The system according to claim 8, wherein the different cross-section channels are randomly situated within the at least one layer of media.

10. The system according to claim 8, wherein the different cross-section channels are situated within the at least one layer of media in an ordered fashion.

11. The system according to claim 1, wherein said at least one layer of the media comprises interrupted channels.

12. The system according to claim 11, wherein all of the layers of the media comprise interrupted channels.

13. The system according to claim 1, wherein the digester is an above-ground digester.

14. The system according to claim 1, wherein the digester is a subterranean digester.

15. The system according to claim 1, wherein the digester is a closed digester.

16. A process for treating flushed waste comprising:
    a) pretreating the flushed waste to remove a portion of the suspended solids;

b) providing an anaerobic digester having a floor and having an upper and lower region; a media of claim 1;

c) directing the flushed waste into the digester via the influent line;

d) passing the flushed waste through the media in the absence of oxygen for a sufficient time to allow the anaerobic microorganisms to digest the organic matter and produce biogas;

e) discharging the treated flushed waste from the digester via the effluent line, and f) collecting and discharging the biogas, wherein said pretreatment step is selected from the group consisting of covered anaerobic lagoon, batch digester, plug-flow digester, completely stirred tank reactor (CSTR), upflow anaerobic sludge blanket, and anaerobic sequencing batch reactor (ASBR).

17. The process according to claim 16, wherein said pretreatment step is selected from the group consisting of: adding chemical compounds to the flushed waste; comminution; and subjecting the flushed waste to biological processes.

18. The process according to claim 16, further comprising the step of heating the flushed waste that is directed into the digester to a temperature higher than 35° C.

19. A fixed-film anaerobic system for treating flushed waste comprising:

a) a digester having a floor and having an upper and a lower region;

b) at least one layer of pliant media supported within the digester, wherein said media consists of immobilized anaerobic microorganisms;

c) an influent line to direct the flushed waste into the digester; and d) an effluent line to remove treated flushed waste from the digester, wherein said pliant media consists of restrained, pliant mesh panels, wherein the pliant mesh panels are restrained on racks, wherein more than one layer of pliant media is supported within the digester tank, wherein said layers comprise at least one layer of media comprising substantially vertically-oriented channels having a first diameter and a first cross-section, and at least another layer of media comprises substantially vertically-oriented channels having a second diameter and a second cross-section, wherein said media immobilizes anaerobic microorganisms.

20. The system according to claim 19, wherein said digester is a subterranean, closed digester and further comprises a means for collecting biogas produced as a by-product of anaerobic digestion of the flushed waste.

21. The system according to claim 19, wherein the second diameter is different from that of the first diameter.

22. The system according to claim 19, wherein the second diameter is substantially similar to that of the first diameter.

* * * * *